(12) United States Patent
Aikawa et al.

(10) Patent No.: US 9,012,482 B2
(45) Date of Patent: Apr. 21, 2015

(54) DRUG CONTAINING BENZOPHENONE DERIVATIVE OR ITS SALT

(75) Inventors: Yukihiko Aikawa, Toyama (JP); Kimiko Morimoto, Toyama (JP); Mari Yamamoto, Toyama (JP); Shunichi Shiozawa, Kobe (JP)

(73) Assignee: Toyama Chemical Co., Ltd., Tokyo (JP)

( * ) Notice: Subject to any disclaimer, the term of this patent is extended or adjusted under 35 U.S.C. 154(b) by 68 days.

(21) Appl. No.: 13/287,375

(22) Filed: Nov. 2, 2011

(65) Prior Publication Data

US 2012/0046326 A1 Feb. 23, 2012

Related U.S. Application Data

(62) Division of application No. 12/679,599, filed as application No. PCT/JP2007/069066 on Sep. 28, 2007, now abandoned.

(51) Int. Cl.
*A61K 31/423* (2006.01)
*A61P 19/10* (2006.01)
*C07D 261/20* (2006.01)

(52) U.S. Cl.
CPC ............ *C07D 261/20* (2013.01); *A61K 31/423* (2013.01)

(58) Field of Classification Search
None
See application file for complete search history.

(56) References Cited

U.S. PATENT DOCUMENTS

| 7,772,285 | B2 | 8/2010 | Chaki et al. |
| 2005/0113400 | A1 | 5/2005 | Chaki et al. |
| 2010/0240891 | A1 | 9/2010 | Aikawa et al. |
| 2011/0020366 | A1 | 1/2011 | Aikawa et al. |
| 2011/0039813 | A1 | 2/2011 | Aikawa et al. |

FOREIGN PATENT DOCUMENTS

WO 2003 042150 5/2003

OTHER PUBLICATIONS

"Osteoporosis: Definition," MayoClinic. Accessed Sep. 11, 2012. Retrieved from <http://www.mayoclinic.com/health/osteoporosis/DS00128>.*
"treatment." (2009). In Mosby's Dictionary of Medicine, Nursing, & Health Professions. Retrieved from <http://www.credoreference.com/entry/ehsmosbymed/treatment> on Nov. 18, 2010.*
Chan, B.Y. et al., "PPAR agonists modulate human osteoclast formation and activity in vitro" BONE, vol. 40, No. 1, pp. 149-159, Jan. 2007.
Takayanagi, Hiroshi, Osteoimmunology and osteoclasts, Journal of Clinical and Experimental Medicine (IGAKU NO AYUMI), vol. 221, No. 1, pp. 37-45, Apr. 7, 2007.
Berenson, James R. et al., "Pathophysiology of Bone Metastases", Cancer Biology & Therapy, vol. 5, Issue 9, pp. 1078-1081, Sep. 2006.

* cited by examiner

*Primary Examiner* — Alicia L Otton
(74) *Attorney, Agent, or Firm* — Oblon, McClelland, Maier & Neustadt, L.L.P.

(57) ABSTRACT

Pharmaceutical agents characterized by containing benzophenone derivatives represented by the general formula:

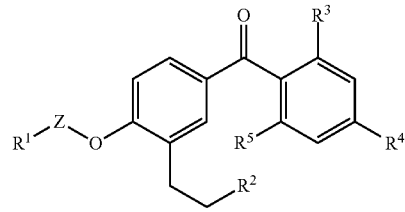

wherein the each substituent is as defined in the specification, or salts thereof have suppressive effect on RANKL production, suppressive effect on OPG reduction and inhibitory effects on differentiation/activation of osteoclasts, and are extremely useful for treating, for example therapy and/or prevention, of various diseases in which differentiation/activation of osteoclast are involved, such as osteoporosis.

3 Claims, No Drawings

DRUG CONTAINING BENZOPHENONE DERIVATIVE OR ITS SALT

CROSS-REFERENCE TO RELATED APPLICATIONS

This application is a divisional of U.S. Ser. No. 12/679,599 filed Jun. 7, 2010, abandoned, which was a National Stage of PCT/JP2007/069066 filed Sep. 28, 2007.

TECHNICAL FIELD

The present invention relates to the pharmaceutical agents containing benzophenone derivatives or salts thereof, which have suppressive effect on RANKL production, suppressive effect on OPG reduction and inhibitory effects on differentiation/activation of osteoclasts, and these are extremely useful as agents for treatment of various diseases in which differentiation/activation of osteoclast are involved, such as osteoporosis.

BACKGROUND ART

Osteoporosis is a systemic disease with bone fragility accompanied by idiopathic dysregulation of bone remodeling which consists in a balance between bone resorption and bone formation. Dysregulation of bone remodeling in osteoporosis results from the enhancement of bone resorption and/or the suppression of bone formation, which occurred systemically. These are independent of presence of local inflammation.

Enhancement of bone resorption is induced by progression of osteoclastogenesis or activation of osteoclasts. Factors promoting osteoclastogenesis such as receptor activator of NF-κB ligand (RANKL) are well known. RANKL promotes osteoclastogenesis and osteoclast activation leading to bone resorption through binding to its receptor, RANK. In addition, osteoprotegerin (OPG) is known as a physiological inhibitor for RANKL and RANK. It has been established that RANK/RANKL/OPG system exerts the central significance on regulation of bone mass (Non-Patent Document 1).

It has been reported that the benzophenone derivatives described in this application have the AP-1 inhibitory effect and are prominent therapeutic agents for autoimmune diseases (Patent Document 1).

However, it has been absolutely unknown that these agents have suppressive effect on RANKL production, suppressive effect on OPG reduction and inhibitory effects on differentiation/activation of osteoclasts.
[Patent Document 1]
International publication WO03/042150 pamphlet
[Non-Patent Document 1]
Cancer Biology and Therapy, 2006, Vol. 5, page 1078-1081.

DISCLOSURE OF THE INVENTION

Problem to be Solved by the Invention

Excellent inhibitor of RANKL production, suppressant of OPG reduction, regulator of RANKL/OPG expression, inhibitor of osteoclast differentiation/activation and pharmaceutical agents for the treatment of osteoporosis with few side-effects are required.

Means to Solve the Problem

Under these conditions, the present inventors have found that pharmaceutical agents containing the benzophenone derivatives represented by the following general formula [1]:

[Formula 1]

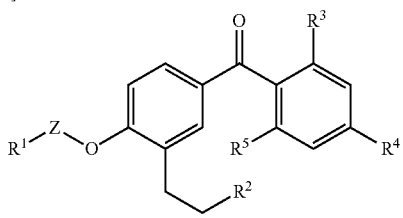

[1]

wherein
$R^1$ represents a substituted or unsubstituted heterocyclic group, a substituted phenyl group or a substituted or unsubstituted alkyl group;
Z represents a substituted or unsubstituted alkylene group;
$R^2$ represents a substituted or unsubstituted heterocyclic group, a substituted or unsubstituted alkoxycarbonyl or heterocyclic carbonyl group or a protected or unprotected carboxyl group;
$R^3$ represents a hydrogen atom, a halogen atom, a cyano group, a nitro group, a protected or unprotected carboxyl group, a protected or unprotected hydroxyl group, a protected or unprotected amino group, a mercapto group, a carbamoyl group or a substituted or unsubstituted alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group;
$R^4$ represents a substituted or unsubstituted alkoxy, cycloalkyloxy, cycloalkenyloxy, alkyl, cycloalkyl, heterocyclic-oxy or heterocyclic group;
$R^5$ represents a hydrogen atom, a halogen atom or a hydroxyl group; or salts thereof are useful as inhibitors of RANKL production, suppressant of OPG reduction, regulator of the expressions of RANKL/OPG, inhibitor of differentiation/activation of osteoclasts and pharmaceutical agents for the treatment of osteoporosis. And they have finally accomplished this invention.

Effect of the Invention

The pharmaceutical agents containing the benzophenone derivatives, represented by the general formula [1] in the present invention, or salts thereof have regulatory effects on the expressions of RANKL/OPG, i.e., suppressive effect on RANKL production, suppressive effect on OPG reduction, and also have inhibitory effects on differentiation/activation of osteoclasts.

Thus these agents are useful as inhibitors of RANKL production, suppressants of OPG reduction, regulators of RANKL/OPG expression and inhibitors of osteoclast differentiation/activation.

Furthermore these treating agents are extremely useful for therapy and/or prevention of the diseases which are induced by overexpression of RANKL or lower expression of OPG, for example, osteoporosis which related with osteoclast differentiation/activation and multiple myeloma, bone metastasis, and so on.

BEST MODE FOR CARRYING OUT THE INVENTION

The present invention will be described in detail below.
In the present specification, the terms have the following meanings, unless otherwise specified.
In this specification, halogen atoms mean fluorine, chlorine, bromine, and iodine atoms; alkyl groups mean straight- or branched-chain $C_{1-12}$ alkyl groups such as methyl, ethyl, n-propyl, isopropyl, n-butyl, sec-butyl, isobutyl, tert-butyl, pentyl, isopentyl, hexyl, heptyl and octyl groups; lower alkyl groups mean straight- or branched-chain $C_{1-6}$ alkyl groups such as methyl, ethyl, n-propyl, isopropyl, n-butyl, sec-butyl, isobutyl, tert-butyl, pentyl and isopentyl groups; halogeno lower alkyl groups mean straight- or branched-chain halogeno-$C_{1-6}$ alkyl groups such as fluoromethyl, chloromethyl, bromomethyl, dichloromethyl, trifluoromethyl, trichloromethyl, chloroethyl, dichloroethyl, trichloroethyl and chloropropyl groups; lower alkoxy lower alkyl groups mean straight- or branched-chain $C_{1-6}$ alkoxy-$C_{1-6}$ alkyl groups such as methoxymethyl, ethoxymethyl, n-propoxymethyl, methoxyethyl and ethoxyethyl groups; hydroxy lower alkyl groups mean straight- or branched-chain hydroxy-$C_{1-6}$ alkyl groups such as hydroxymethyl, hydroxyethyl and hydroxypropyl groups; amino lower alkyl groups mean amino-$C_{1-6}$ alkyl groups such as aminomethyl, aminoethyl and aminopropyl groups.

Alkenyl groups mean straight- or branched-chain $C_{2-12}$ alkenyl groups such as vinyl, allyl, propenyl, isopropenyl, butenyl, isobutenyl, pentenyl, hexenyl, heptenyl and octenyl groups; lower alkenyl groups mean straight- or branched-chain $C_{2-6}$ alkenyl groups such as vinyl, allyl, propenyl, isopropenyl, butenyl, isobutenyl and pentenyl groups.

Cycloalkyl groups mean $C_{3-7}$ cycloalkyl groups such as cyclopropyl, cyclobutyl, cyclopentyl, cyclohexyl or cycloheptyl group; cycloalkyloxy groups mean $C_{3-7}$ cycloalkyloxy groups such as cyclopropyloxy, cyclobutyloxy, cyclopentyloxy, cyclohexyloxy or cyclopentyloxy group; cycloalkenyloxy groups mean $C_{5-7}$ cycloalkenyloxy groups such as cyclopentenyloxy and cyclohexenyloxy groups.

Aryl groups mean, for example, phenyl, tolyl and naphthyl groups; aralkyl groups mean ar-$C_{1-12}$ alkyl groups such as benzyl, diphenylmethyl, trityl, phenethyl, 4-methylbenzyl and naphthylmethyl groups; Aryloxy groups mean, for example, phenoxy and naphthoxy groups; aryloxycarbonyl groups mean, for example, phenoxycarbonyl and naphthoxycarbonyl groups.

Alkoxy groups mean straight- or branched-chain $C_{1-12}$ alkoxy groups such as methoxy, ethoxy, n-propoxy, isopropoxy, n-butoxy, isobutoxy, sec-butoxy, tert-butoxy, pentyloxy, isopentyloxy, hexyloxy, heptyloxy and octyloxy groups; lower alkoxy groups mean straight- or branched-chain $C_{1-6}$ alkoxy groups such as methoxy, ethoxy, n-propoxy, isopropoxy, n-butoxy, isobutoxy, sec-butoxy, tert-butoxy, pentyloxy and isopentyloxy groups; alkoxyalkyl groups mean, for example, methoxymethyl, methoxyethyl methyl and 2-(trimethylsilyl)ethoxymethyl group.

Alkylene groups mean straight- or branched-chain $C_{1-12}$ alkylene groups such as methylene, ethylene and propylene groups.

Alkoxycarbonyl groups mean straight- or branched-chain $C_{1-12}$ alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and pentyloxycarbonyl groups; lower alkoxycarbonyl groups mean straight- or branched-chain $C_{1-6}$ alkyloxycarbonyl groups such as methoxycarbonyl, ethoxycarbonyl and propoxycarbonyl groups; lower alkoxycarbonyl lower alkyl groups mean straight- or branched-chain $C_{1-6}$ alkoxycarbonyl-$C_{1-6}$ alkyl groups such as methoxycarbonylmethyl, ethoxycarbonylmethyl, n-propoxycarbonylmethyl, methoxycarbonylethyl and ethoxycarbonylethyl groups; ar-alkyloxycarbonyl groups mean ar-$C_{1-12}$ alkyloxycarbonyl groups such as benzyloxycarbonyl and 4-methylbenzyloxycarbonyl groups.

Lower alkoxyimino groups mean straight- or branched-chain $C_{1-6}$ alkoxyimino groups such as methoxyimino and ethoxyimino groups; alkylamino groups mean straight- or branched-chain $C_{1-12}$ alkylamino groups such as methylamino, ethylamino, propylamino, butylamino, pentylamino, hexylamino, heptylamino and octylamino groups; lower alkylamino groups mean straight- or branched-chain mono- or di-$C_{1-6}$ alkylamino groups such as methylamino, ethylamino, propylamino, dimethylamino, diethylamino and methylethylamino groups; lower alkylamino lower alkyl groups mean mono- or di-$C_{1-6}$ alkylamino-$C_{1-6}$ alkyl groups such as methylaminomethyl, methylaminoethyl, ethylaminomethyl, methylaminopropyl, propylaminoethyl, dimethylaminomethyl, diethylaminomethyl, diethylaminoethyl and dimethylaminopropyl groups; lower alkylidene groups mean $C_{1-6}$ alkylidene groups such as methylene, ethylidene, propylidene and isopropylidene groups.

Nitrogen-containing heterocyclic groups mean 5- or 6-membered-ring, condensed-ring or bridged-ring heterocyclic groups each of which contains one or more nitrogen atoms as hetero atoms forming the ring and optionally one or more oxygen atoms or sulfur atoms, such as pyrrolyl, pyrrolidinyl, piperidyl, piperazinyl, imidazolyl, pyrazolyl, pyridyl, tetrahydropyridyl, pyrimidinyl, morpholinyl, thiomorpholinyl, quinolyl, quinolizinyl, tetrahydroquinolinyl, tetrahydroisoquinolinyl, quinuclidinyl, quinazolyl, thiazolyl, tetrazolyl, thiadiazolyl, pyrrolinyl, imidazolinyl, imidazolidinyl, pyrazolinyl, pyrazolidinyl, purinyl and indazolyl groups.

Heterocyclic groups mean the above described nitrogen-containing heterocyclic groups and 5- or 6-membered-ring, condensed-ring or bridged-ring heterocyclic groups each of which contains at least one or more heteroatoms selected from the group consisting of nitrogen, oxygen and sulfur atoms and optionally one or more oxygen and sulfur atoms as heteroatoms forming the ring, such as furyl, thienyl, 4-methyl-2-oxo-1,3-dioxol, benzothienyl, pyranyl, isobenzofuranyl, oxazolyl, benzofuranyl, indolyl, benzimidazolyl, benzoxazolyl, benzisoxazolyl, benzothiazolyl, quinoxalyl, dihydroquinoxalinyl, 2,3-dihydrobenzothienyl, 1,3-dihydrobenzopyrrolyl, 1,3-dihydro-4H-1-thianaphthyl, 2,3-dihydrobenzofuranyl, benzo[b]dioxanyl, imidazo[2,3-a]pyridyl, benzo[b]piperazinyl, chromenyl, isothiazolyl, isoxazolyl, thiadiazolyl, oxadiazolyl, pyridazinyl, isoindolyl and isoquinolyl groups; heterocyclic carbonyl groups mean heterocyclic-CO-groups such as 4-hydroxy-2-(5H)-furanocarbonyl, morpholinocarbonyl, piperazinocarbonyl or pyrrolidinocarbonyl group.

Acyl groups mean, for example, formyl group, straight- or branched-chain $C_{2-12}$ alkanoyl groups such as acetyl, isovaleryl, propionyl and pivaloyl, aralkylcarbonyl groups such as benzylcarbonyl group, aroyl groups such as benzoyl and naphthoyl groups, and heterocyclic carbonyl groups such as nicotinoyl, thenoyl, pyrrolidinocarbonyl and furoyl groups; acylamino groups mean $C_{1-6}$ acylamino groups such as formylamino, acetylamino, propionylamino and butyrylamino groups; alkanoyloxy groups mean $C_{2-12}$ alkanoyloxy group such as acetyloxy, propionyloxy and pivaloyloxy groups.

Cyclic amino groups mean both saturated and unsaturated cyclic amino groups, each of which optionally contains, in the ring, one or more heteroatoms such as nitrogen, oxygen and sulfur atoms and carbonyl-carbons and may be monocyclic or di- to tricyclic, in more particular, saturated or unsaturated 3- to 7-membered-ring monocyclic amino groups containing one nitrogen atom, such as aziridin-1-yl, azetizin-1-yl, pyrrolidin-1-yl, pyrrolin-1-yl, pyrrol-1-yl, dihydropyridin-1-yl, piperidin-1-yl, dihydroazepin-1-yl and perhydroazepin-1-yl groups, saturated or unsaturated 3- to 7-membered-ring monocyclic amino groups containing two nitrogen atoms, such as imidazol-1-yl, imidazolidin-1-yl, imidazolin-1-yl, pyrazolidin-1-yl, piperazin-1-yl, 1,4-dihydropyrazin-1-yl, 1,2-dihydropyrimidin-1-yl, perhydropyrazin-1-yl and homopiperazin-1-yl groups, saturated or unsaturated 3- to 7-membered-ring monocyclic amino groups containing 3 or more nitrogen atoms, such as 1,2,4-triazol-1-yl, 1,2-dihydro-1,2,4-triazin-1-yl and perhydro-5-triazin-1-yl, saturated or unsaturated 3- to 7-membered-ring monocyclic amino groups containing 1 to 4 heteroatoms selected from the group consisting of oxygen and sulfur atoms, besides nitrogen atoms, such as oxazolidin-3-yl, isoxazolidin-2-yl, morpholin-4-yl, thiazolidin-3-yl, isothiazolidin-2-yl, thiomorpholin-4-yl, homothiomorpholin-4-yl and 1,2,4-thiaziazolidin-2-yl groups, saturated or unsaturated di- to tricyclic amino groups such as isoindolin-2-yl, indolin-1-yl, 1H-indazol-1-yl, purin-7-yl and tetrahydroquinolin-1-yl groups, and spiro or bridged saturated or unsaturated 5- to 12-membered cyclic amino groups such as 5-azaspiro[2.4]heptan-5-yl, 2,8-diazabicyclo[4.3.0]nonan-8-yl, 3-azacyclo[3.1.0]hexan-3-yl, 2-oxa-5,8-diazabicyclo[4.3.0]nonan-8-yl, 2,8-diazaspiro[4.4]nonan-2-yl and 7-azabicyclo[2.2.1]heptan-7-yl groups.

Alkylthio groups mean straight- or branched-chain $C_{1-12}$ alkylthio groups such as methylthio, ethylthio, n-propylthio, isopropylthio, n-butylthio, isobutylthio, sec-butylthio, tert-butylthio, pentylthio, isopentylthio, hexylthio, heptylthio and octylthio groups; lower alkylthio groups mean straight- or branched-chain $C_{1-6}$ alkylthio groups such as methylthio, ethylthio, n-propylthio, isopropylthio, n-butylthio, isobutylthio, sec-butylthio, tert-butylthio, pentylthio and isopentylthio groups.

Alkylsulfinyl groups mean straight- or branched-chain $C_{1-12}$ alkylsulfinyl groups such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl, isopentylsulfinyl, hexylsulfinyl, heptylsulfinyl and octylsulfinyl groups; alkylsulfonyl groups mean straight- or branched-chain $C_{1-12}$ alkylsulfonyl groups such as methylsulfonyl, ethylsulfonyl, n-propylsulfonyl, isopropylsulfonyl, n-butylsulfonyl, isobutylsulfonyl, sec-butylsulfonyl, tert-butylsulfonyl, pentylsulfonyl, isopentylsulfonyl, hexylsulfonyl, heptylsulfonyl and octylsulfonyl groups; arylsulfonyl groups mean, for example, benzenesulfonyl and p-toluenesulfonyl groups.

Alkylsulfonylamino groups mean straight- or branched-chain $C_{1-12}$ alkylsulfonylamino groups such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino, pentylsulfonylamino, isopentylsulfonylamino, hexylsulfonylamino, heptylsulfonylamino and octylsulfonylamino groups; arylsulfonylamino groups mean aryl-SO$_2$NH-groups such as phenylsulfonylamino and naphthylsulfonylamino groups.

Lower alkylsulfinyl groups mean straight- or branched-chain $C_{1-6}$ alkylsulfinyl groups such as methylsulfinyl, ethylsulfinyl, n-propylsulfinyl, isopropylsulfinyl, n-butylsulfinyl, isobutylsulfinyl, sec-butylsulfinyl, tert-butylsulfinyl, pentylsulfinyl and hexylsulfinyl groups; lower alkylsulfonyl groups mean straight- or branched-chain $C_{1-6}$ alkylsulfonyl groups such as methylsulfonyl, ethylsulfonyl, n-propylsulfonyl, isopropylsulfonyl, n-butylsulfonyl, isobutylsulfonyl, sec-butylsulfonyl, tert-butylsulfonyl and pentylsulfonyl.

Lower alkylcarbamoyl groups mean mono- or di-$C_{1-6}$ alkylcarbamoyl groups such as methylcarbamoyl, ethylcarbamoyl, propylcarbamoyl, dimethylcarbamoyl, diethylcarbamoyl and methylethylcarbamoyl groups; lower alkylsulfonylamino groups mean straight- or branched-chain $C_{1-6}$ alkylsulfonylamino groups such as methylsulfonylamino, ethylsulfonylamino, n-propylsulfonylamino, isopropylsulfonylamino, n-butylsulfonylamino, isobutylsulfonylamino, sec-butylsulfonylamino, tert-butylsulfonylamino and pentylsulfonylamino groups.

Lower alkylsulfonylcarbamoyl groups mean straight- or branched-chain $C_{1-6}$ alkylsulfonylcarbamoyl groups such as methylsulfonylcarbamoyl, ethylsulfonylcarbamoyl, n-propylsulfonylcarbamoyl, isopropylsulfonylcarbamoyl, n-butylsulfonylcarbamoyl, isobutylsulfonylcarbamoyl, sec-butylsulfonylcarbamoyl, tert-butylsulfonylcarbamoyl and pentylsulfonylcarbamoyl groups; lower alkylaminosulfonyl groups mean mono- or di-$C_{1-6}$ alkylaminosulfonyl groups such as methylaminosulfonyl, ethylaminosulfonyl, propylaminosulfonyl, dimethylaminosulfonyl, diethylaminosulfonyl and methylethylaminosulfonyl groups.

Carboxyl-lower alkenyl groups mean, for example, straight- or branched-chain carboxyl-substituted $C_{2-6}$ alkenyl groups.

Lower alkyl-heterocyclic groups mean, for example, heterocyclic groups substituted with a straight- or branched-chain lower alkyl group.

Lower alkoxy-lower alkoxy groups mean straight- or branched-chain $C_{1-6}$ alkoxy groups substituted with a lower alkoxy group.

Leaving groups mean halogen atoms, alkylsulfonyloxy groups such as methylsulfonyloxy group, and arylsulfonyloxy groups such as p-toluenesulfonyloxy and benzenesulfonyloxy groups; and heterocyclic oxy groups mean groups represented by heterocyclic-O— each of which binds via an oxygen atom, such as pyrrolidinyloxy, piperidinyloxy, tetrahydrofuranyloxy, tetrahydropyranyloxy and tetrahydrothiopyranyloxy groups.

The amino protecting group includes any group which can be normally used as a protecting group of an amino group, and examples thereof include groups described in W. Greene et al., Protective Groups in Organic Synthesis, third edition, pp. 494-615, 1999, John Wiley & Sons, INC. Specific examples thereof include an acyl group, an alkoxycarbonyl group, an aralkyloxycarbonyl group, an aryloxycarbonyl group, an aralkyl group, an alkoxyalkyl group, an alkylsulfonyl group and an arylsulfonyl group.

The hydroxyl protecting group includes any group which can be normally used as a protecting group of a hydroxyl group, and examples thereof include groups described in W. Greene et al., Protective Groups in Organic Synthesis, third edition, pp. 17-245, 1999, John Wiley & Sons, INC. Specific examples thereof include an acyl group, an alkoxycarbonyl group, an aralkyloxycarbonyl group, an alkyl group, an alkenyl group, an aralkyl group and an alkoxyalkyl group.

The carboxyl protecting group includes any group which can be normally used as a protecting group of a carboxyl group, and examples thereof include groups described in W. Greene et al., Protective Groups in Organic Synthesis, third edition, pp. 369-453, 1999, John Wiley & Sons, INC. Specific examples thereof include an alkyl group, an alkenyl group, an aryl group, an aralkyl group, a cycloalkyl group and an alkoxyalkyl group.

Phosphoryl protecting group includes any group which can be normally used as a protecting group of a phosphoryl group, for example, alkyl group, alkenyl group, aralkyl group and aryl group.

Sulfo protecting group includes any group which can be normally used as a protecting group of a sulfonyloxy group, for example, aryl group and alkyl group.

Each substituent of the heterocyclic groups, phenyl and alkyl groups of the groups $R^1$, heterocyclic, alkoxycarbonyl, heterocyclic carbonyl groups of the groups $R^2$, alkyl, alkenyl, cycloalkyl, aryl, aralkyl, alkoxy, aryloxy, acyl, alkoxycarbonyl, aryloxycarbonyl, alkylthio, alkylsulfinyl, alkylsulfonyl, alkylamino, acylamino, alkylsulfonylamino, arylsulfonylamino or heterocyclic group of the groups $R^3$, or alkoxy, cycloalkyloxy, cycloalkenyloxy, alkyl, cycloalkyl, heterocyclic oxy or heterocyclic group of the groups $R^4$ is optionally substituted with one or more groups selected from the group consisting of a cyano group, a nitro group, a halogen atom, an unprotected or protected carboxyl, phosphoryl, hydroxyl, amino, carbamoyl, hydroxycarbamoyl, aminosulfonyl, sulfo, hydroxy lower alkyl, amino lower alkyl, cyclic amino, lower alkylamino and lower alkylamino lower alkyl group, a lower alkyl group, a lower alkenyl group, lower alkoxy group, a lower alkoxycarbonyl group, an acyl group, an aryl group, a heterocyclic group, a cycloalkyl group, an aralkyl group, a lower alkylidene group, a mercapto group, a lower alkylthio group, a lower alkylsulfinyl group, a lower alkylsulfonyl group, a lower alkylsulfonylcarbamoyl group, a lower alkylcarbamoyl group, a lower alkylsulfonylamino group, a lower alkylaminosulfonyl group, a carboxyl lower alkenyl group, a hydroxyheterocyclic group, a lower alkyl heterocyclic group, a lower alkoxy lower alkoxy group, a halogeno lower alkyl group, a lower alkoxy lower alkyl group, a lower alkoxycarbonyl lower alkyl group, and a lower alkoxyimino group.

The alkylene group of Z is optionally substituted with one or more groups selected from the group consisting of a cyano group, a nitro group, a halogen atom, an unprotected or protected carboxyl, carbamoyl, hydroxycarbamoyl, hydroxy lower alkyl, amino lower alkyl and lower alkylamino lower alkyl group, a lower alkyl group, a lower alkoxycarbonyl group, an acyl group, an aryl group, heterocyclic group, a cycloalkyl group, a lower alkenyl group, an aralkyl group, a lower alkylsulfonylcarbamoyl group, a lower alkylcarbamoyl group, a halogeno lower alkyl group, a lower alkoxy lower alkyl group, and a lower alkoxycarbonyl lower alkyl group.

Salts of the compounds having general formula [1] include, for example, commonly known salts produced in the compounds' basic groups such as amino group and produced in the compounds' acidic groups such as hydroxyl and carboxyl groups.

Salts produced in the compounds' basic groups include, for example, salts produced with mineral acids such as hydrochloric acid, hydrobromic acid, nitric acid and sulfuric acid; salts produced with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts produced with sulfonic acids such as methanesulfonic acid, benzenesulfonic acid, p-toluenesulfonic acid, mesitylenesulfonic acid and naphthalenesulfonic acid.

Salts produced in the compounds' acidic groups include, for example, salts produced with alkaline metals such as sodium and potassium; salts produced with alkaline earth metals such as calcium and magnesium; ammonium salts; and salts produced with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

In the salts mentioned above, preferable salts are pharmacologically acceptable salts.

When isomers (e.g. optical isomers, geometrical isomers and tautomers) are present in compounds having the general formula [1] or the salts thereof, this invention embraces the isomers. This invention also embraces the solvates, the hydrates and the crystals in various forms of the compound or the salt thereof.

The preferable compounds having the general formula [1] or the salts thereof are as follows.

In the compounds of this invention, $R^1$ is preferably a substituted or unsubstituted heterocyclic group or a substituted phenyl group, more preferably an optionally substituted heterocyclic group.

In the compounds of this invention, $R^2$ is preferably a carboxyl group that may be protected with an alkyl group, more preferably a carboxyl group.

In the compounds of this invention, $R^3$ is preferably a protected or unprotected hydroxyl group, more preferably a hydroxyl group.

In the compounds of this invention, $R^4$ is preferably a substituted or unsubstituted cycloalkyloxy group, more preferably a cycloalkyloxy group.

In the compounds of this invention, $R^5$ is preferably a hydrogen atom.

In the compounds of this invention, Z is preferably an alkylene group, more preferably a methylene group.

For the benzophenone derivatives of the general formula [1] or salts thereof, 2-(4-morpholinyl)ethyl 3-(5-(4-(cyclopentyloxy)-2-hydroxybenzoyl)-2-((3-hydroxy-1,2-benzisoxazol-6-yl)methoxy)phenyl)propionate, 4-((2-(2-carboxyethyl)-4-(4-(cyclopentyloxy)-2-hydroxybenzoyl)phenoxy)methyl)benzoic acid, 3-(5-(4-(cyclopentyloxy)-2-hydroxybenzoyl)-2-((4-(3-hydroxy-5-isoxazolyl)benzyl)oxy)phenyl)propionic acid and 3-(5-(4-(cyclopentyloxy)-2-hydroxybenzoyl)-2-((3-hydroxy-1,2-benzisoxazol-6-yl)methoxy)phenyl)propionic acid or the salt are preferable, and 3-(5-(4-(cyclopentyloxy)-2-hydroxybenzoyl)-2-((3-hydroxy-1,2-benzisoxazol-6-yl)methoxy)phenyl)propionic acid or the salt is more preferable.

The pharmaceutical agents containing the benzophenone derivatives, represented by the general formula [1] in the present invention, or salts thereof have regulatory effects on the expressions of RANKL/OPG, i.e., suppressive effect on RANKL production, suppressive effect on OPG reduction, and also have inhibitory effects on differentiation/activation of osteoclasts.

Thus these agents are useful as inhibitors of RANKL production, suppressors of OPG reduction, regulators of RANKL/OPG expression and inhibitors of osteoclast differentiation/activation.

Furthermore these agents are useful for therapy and/or prevention of the diseases which are induced by overexpression of RANKL or lower expression of OPG, for example, osteoporosis which related with osteoclast differentiation/activation and multiple myeloma, bone metastasis, and so on, more preferably these agents are useful for therapy and/or prevention of osteoporosis. And these agents are more useful for therapy.

The benzophenone derivatives represented by the general formula [1] or salts thereof are produced by known methods or combining known methods or the methods described in Patent Document 1.

The benzophenone derivatives represented by the general formula [1] or salts thereof can be formulated into pharmaceutical preparations such as oral agents (a tablet, a capsule, a powder, a granule, a fine powder, a pill, a suspension, an emulsion, a solution, a syrup, etc.), or injections, by adding thereto various types of pharmaceutical additives such as an excipient, a binder, a disintegrator, a disintegration inhibitor, an anticaking/antiadhesion agent, a lubricant, an absorption/adsorption carrier, a solvent, an extender, an isotonizing agent, a solubilizer, an emulsifier, a suspending agent, a thickener, a coating agent, an absorbefacient, a gelation/agglutination promoter, a light stabilizer, a preservative, an anti-moisture agent, an emulsion/suspension/dispersion stabilizer, a coloration preventing agent, a deoxidizer/antioxidant, correctives, a coloring agent, a whipping agent, an antifoaming agent, a soothing agent, an antistatic agent, or a buffer/pH adjuster.

The aforementioned various types of agents are formulated by common methods.

Oral solid preparations such as a tablet, a powder, or a granule may be prepared according to common methods, using the following pharmaceutical additives for such solid preparations, for example: excipients such as lactose, sucrose, sodium chloride, glucose, starch, calcium carbonate, kaolin, crystalline cellulose, anhydrous dibasic calcium phosphate, partly pregelatinized starch, corn starch, or alginic acid; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, sodium alginate, gum Arabic, hydroxypropylmethylcellulose, hydroxypropylcellulose, water, or ethanol; disintegrators such as dry starch, alginic acid, agar powders, starch, crosslinked polyvinylpyrrolidone, crosslinked carboxymethylcellulose sodium, carboxymethylcellulose calcium, or sodium starch glycolate; disintegration inhibitors such as stearyl alcohol, stearic acid, cacao butter, or hydrogenated oil; anticaking/antiadhesion agents such as aluminum silicate, calcium hydrogen phosphate, magnesium oxide, talc, or silicic acid anhydride; lubricants such as carnauba wax, light anhydrous silicic acid, aluminum silicate, magnesium silicate, hardened oil, hardened vegetable oil derivative, sesame oil, white beeswax, titanium oxide, dry aluminum hydroxide gel, stearic acid, calcium stearate, magnesium stearate, talc, calcium hydrogen phosphate, sodium lauryl sulfate, or polyethylene glycol; absorption promoters such as quaternary ammonium salts, sodium lauryl sulfate, urea, or enzyme; and absorption/adsorption carriers such as starch, lactose, kaolin, bentonite, silicic acid anhydride, hydrous silicon dioxide, magnesium aluminometasilicate, or colloidal silicic acid.

Moreover, as necessary, a tablet may be processed into a tablet coated with a common coating agent, such as a sugar-coated tablet, a gelatin-coated tablet, a gastric coated tablet, an enteric coated tablet, and a water-soluble film coated tablet.

A capsule is prepared by mixing the present compound with the aforementioned various types of pharmaceuticals and filling the obtained mixture in a hard gelatin capsule or soft capsule.

Furthermore, the compound of the present invention may also be formulated into water- or oil-type suspension, solution, syrup, and elixir, by common methods, using the aforementioned various types of additives for liquid preparations, such as a solvent, an extender, an isotonizing agent, a solubilizer, an emulsifier, a suspending agent, or a thickener.

An injection may be prepared by common methods, using pharmaceutical additives for liquid preparations including: diluents such as water, ethyl alcohol, Macrogol, propylene glycol, citric acid, acetic acid, phosphoric acid, lactic acid, sodium lactate, sulfuric acid, sodium hydroxide; pH adjusters and buffers, such as sodium citrate, sodium acetate, or sodium phosphate; stabilizers such as sodium pyrosulfite, ethylenediaminetetraacetic acid, thioglycolic acid, or thiolactic acid; isotonizing agents such as salts (sodium chloride), glucose, mannitol, or glycerin; solubilizers such as carboxymethylcellulose sodium, propylene glycol, sodium benzoate, benzyl benzoate, urethane, ethanolamine, or glycerin; soothing agents such as calcium gluconate, chlorobutanol, glucose, or benzyl alcohol; and local anesthetics.

A method for administration of the aforementioned preparations is not particularly limited. It is determined as appropriate, depending on the form of a preparation, the age of a patient, the sex thereof, and the degree of the symptoms of a patient, and other conditions.

The dosage of the active ingredient of the preparation of the present invention is selected as appropriate, depending on the usage, the age of a patient, the sex thereof, the form of disease, and other conditions. In general, the present preparation may be administered at a dosage between 1 and 1500 mg per adult per day, once or divided over several administrations.

EXAMPLES

The present invention will be described in the following test examples and formulation examples. However, these examples are not intended to limit the scope of the present invention.

In this test example, 3-(5-(4-(cyclopentyloxy)-2-hydroxybenzoyl)-2-(3-hydroxy-1,2-benzisoxazol-6-yl)methoxy)phenyl)propionic acid (hereinafter called as "T-5224") was used as a test compound.

Test Example 1

The Effect of T-5224 on the Expressions of RANKL and OPG

Male DBA/1 J mice at 8-week old (Charles River Laboratories Japan, Inc.) were used. Bovine type II collagen (KO-KEN CO., LTD.) dissolved at 2 mg/mL in 0.1 mol/L acetic acid was mixed and emulsified with an equal volume of Freund's complete adjuvant (Difco Laboratories, Inc.), and then 0.2 mL of the emulsion was intradermally injected at the tail head of each mouse. The same treatment was carried out 21 days after the first immunization so that type II collagen-induced arthritis was induced in mice. T-5224 was dissolved in the 2-fold molar amount of sodium hydroxide solution, and then water and polyvinylpyrrolidone (PVP) at 3-fold weight of T-5224 were added to yield 3 mg/mL of T-5224-dosing solution. T-5224 at 30 mg/kg was orally administered once daily from 21 to 34 days after the first immunization. PVP solution was administered to the mice in Control group.

On the next day of final administration, the hind paws were collected. After the excision of claws and skin, they were immersed in RNA-stabilizing agent (RNAlater, Ambion, Inc.) and kept in a refrigerator overnight. Then RNA-stabilizing agent was wiped up, and the hind paws were cryopreserved and crushed by pressing under cooling with the liquid nitrogen. Each crushed sample was homogenized in cell lysis reagent (QIAzol lysis reagent, QIAGEN GmbH) and RNA was isolated from each sample using RNA isolation kit (RNeasy lipid tissue mini kit, QIAGEN GmbH). Ten micrograms of RNA was mixed with 100 units of reverse transcriptase (ReverTra Ace, Toyobo Co., Ltd.), 4 µL of 5× reaction buffer (an attachment in reverse transcriptase, Toyobo Co., Ltd.), 0.8 µL of 25 mmol/L dNTPs (Toyobo Co., Ltd.), 5 µmol of oligo(dT)$_{20}$ (Toyobo Co., Ltd.) and RNase-free water (Takara Bio Inc.) in total volume of 20 µL per sample, and the reaction mixtures were incubated at 42° C. for 1 hr and at approximately 95° C. for 5 min to yield reverse transcription (RT) products.

RT product (100 ng, equivalent amount to RNA) was mixed with 25 µL of quantitative PCR reagent (qPCR Mastermix, Eurogentec S.A.), 2.5 μL of probe/primer solution (TaqMan gene expression assays tumor necrosis factor (ligand) superfamily member 11 *Mus musculus*, Applied Biosystems) and RNase-free water (Takara Inc.) in total volume of 50 μL, and then PCR reaction (hold at 50° C. for 2 min, hold at 95° C. for 10 min, 40 cycles at 95° C. for 15 sec and at 60° C. for 1 min) was carried out using real-time PCR system (ABI PRISM 7700 sequence detection system, Applied Biosystems) to measure RANKL mRNA. Similarly, RT product (10 ng, equivalent amount to RNA) and probe/primer solution (TaqMan Gene expression assays tumor necrosis factor receptor superfamily member 11b Mus musculus, Applied Biosystems) were used to measure OPG mRNA, and RT product (100 ng, equivalent amount to RNA) and probe/primer solution (TaqMan gene expression assays hypoxanthine guanine phosphoribosyl transferase 1 *Mus musculus*, Applied Biosystems) were used to measure Hprt1 mRNA. The levels of RANKL mRNA and OPG mRNA were expressed as the normalized ratio to Hprt1 mRNA amount. The result is shown in Table 1.

TABLE 1

|  | RANKL | OPG |
| --- | --- | --- |
| Normal group | 0.096 | 0.375 |
| Control group | 0.927 | 0.156 |
| Treatment group | 0.224 | 0.306 |

Treatment of T-5224 inhibited the increase of RANKL mRNA level and the decrease of OPG mRNA level by 84% and 68%, respectively.

T-5224 showed the regulatory effect with controlling the expression of RANKL/OPG to normal level in hind paws of mice with type II collagen-induced arthritis.

Test Example 2

The Effect of T-5224 on Osteoporosis in Femur of Mouse

The induction of mouse type II collagen-induced arthritis and the preparation of T-5224-dosing solution (1 mg/mL) were carried out by the same procedure in Example 1. T-5224 at 10 mg/kg was orally administered once daily from 21 to 49 days after the first immunization. PVP solution was administered to the mice in Control group.

The femora isolated on the next day of final administration were fixed with formalin, and then scanned using μCT scanner system (MCT-100CB, Hitachi, Ltd.) (X-ray tube voltage: 90.0 kV, X-ray tube current: 100 iris: 3630, magnification: ×5, resolution: 30 μm). Bone density was evaluated as CT value using 3D CT image ("img" format) assembled by μCT scanner system and bone morphometry software (TRI-3D/BON, Ratoc System Engineering Co., Ltd.) according to the manufacturer's protocol. The evaluation site was set on a metaphyseal slice with 0.35 mm thickness at a point 3% of the length of the femur from the distal growth plate, according to the report of Jochems C. et al. [Arthritis Research and Therapy, 2005, Vol. 7, page R837-R843]. The result is shown in Table 2.

TABLE 2

|  | CT Value |
| --- | --- |
| Normal group | 761 |
| Control group | 657 |
| Treatment group | 708 |

The CT value in Control group decreased to 86% of the value in Normal group. On the other hand, the treatment of T-5224 inhibited the reduction of CT value by 49% and showed the suppressive effect on the decrease of bone density.

T-5224 inhibited the development of osteoporosis in femora which was non-arthritic region of mice with type II collagen-induced arthritis.

Formulation Example 1

20 g of T-5224, 21.5 g of Polyvinylpyrrolidone K-30 (trade name: Plasdone K29/32, ISP), 73.0 g of humidified L-Arginine (Ajinomoto), and 121.5 g of milled mannitol for direct compression (trade name: Parteck M100, Merck), 4.7 g of sodium carboxymethyl starch (trade name: Primojel, Matsutani Kagaku), and 4.6 g of magnesium stearate were weighted and mixed. After passing them through 30 mesh-sieve, they were mixed and the powder for tablet was obtained. After tabletting with a punch 8.5 mm in diameter, they were dried at 50° C. and 20 mg content of T-5224 tablet with 230 mg of a tablet weight was obtained.

Formulation Example 2

1 g of T-5224 was dissolved by 7.7 mL of 0.5 mol/L sodium hydroxide and 10 mL of purified water. 3 g of Polyvinylpyrrolidone K-30 (Plasdone K29/32, ISP) is dissolved in this solution, and 50 mg/mL content of T-5224 solution with pH 8.1 was obtained.

INDUSTRIAL APPLICABILITY

The pharmaceutical agents containing the benzophenone derivatives or salts thereof in the present invention have suppressive effect on RANKL production, suppressive effect on OPG reduction and inhibitory effects on differentiation/activation of osteoclasts, and are extremely useful for treatment and/or prevention of various diseases in which differentiation/activation of osteoclast are involved, such as osteoporosis.

The invention claimed is:
1. A method for therapy of osteoporosis in a non-arthritic region, comprising administering to a subject in need thereof a benzophenone derivative in an amount of 30 mg/kg/day, wherein the osteoporosis is induced by overexpression of receptor activator of NF-κB ligand (RANKL) or lower expression of osteoprotegerin (OPG), and the benzophenone derivative is 3-(5 -(4 -(cyclopentyloxy)-2-hydroxybenzoyl)-2-((3-hydroxy-1,2-benzisoxazol-6-yl)methoxy)phenyl)propionic acid.
2. The method for therapy of osteoporosis according to claim 1, wherein the osteoporosis is induced by overexpression of receptor activator of NF-κB ligand (RANKL).
3. The method for therapy of osteoporosis according to claim 1, wherein the osteoporosis is induced by lower expression of osteoprotegerin (OPG).

* * * * *